United States Patent [19]

Acton et al.

[11] Patent Number: 5,064,824
[45] Date of Patent: Nov. 12, 1991

[54] CEPHALOSPORIN COMPOUNDS

[75] Inventors: David G. Acton, Rudheath; David H. Davies, Sutton; Jeffrey P. Poyser, Handforth, all of England

[73] Assignee: Imperial Chemical Industries PLC, London, England

[21] Appl. No.: 347,567

[22] Filed: May 5, 1989

[30] Foreign Application Priority Data

May 10, 1988 [GB] United Kingdom ............... 8811056

[51] Int. Cl.$^5$ ................. C07D 501/22; A61K 31/545
[52] U.S. Cl. ..................................... 514/202; 514/201; 514/206; 540/221; 540/222; 540/225
[58] Field of Search ............... 540/225, 222, 221; 514/202, 201, 206, 204

[56] References Cited
PUBLICATIONS
CA 111 96959(d) (1989).

Primary Examiner—Nicholas S. Rizzo
Attorney, Agent, or Firm—Cushman, Darby & Cushman

[57] ABSTRACT

Cephalosporin antibiotics having a 3-position substituent of the formula:

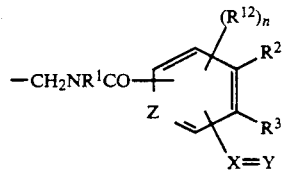

are described; wherein $R^1$ is hydrogen or certain substituted alkyl groups, Z is CH or N, $R^2$ and $R^3$ are hydroxy or in vivo hydrolysable esters thereof, $(R^{12})_n$ represents various optional substituents and X=Y is an olefin, oxime, azo or related group. Processes for their preparation and use are described.

8 Claims, No Drawings

CEPHALOSPORIN COMPOUNDS

The present invention relates to cephalosporins and in particular to such compounds comprising an amide group. This invention further relates to processes for their preparation, to intermediates in their preparation, to their use as therapeutic agents and to pharmaceutical compositions containing them. The compounds of this invention are antibiotics and can be used in the treatment of any disease that is conventionally treated with antibiotics for example in the treatment of bacterial infection in mammals including humans. The compounds of this invention also have non-therapeutic uses as they can be used in conventional manner in industry for example they can be used as disinfectants and food preservatives. The compounds of this invention, however, are primarily of therapeutic interest as they show a desirable profile of activity in their antibacterial effect.

Investigation into new cephalosporin derivatives has been intense over the past 25 years with many thousands of patents and scientific papers having been published. A particular problem associated with the commercially available cephalosporins is the lack of potency against strains of Pseudomonas. The present invention provides cephalosporin derivatives having novel 3-position substituents, which derivatives possess good antibacterial activity and in particular against strains of Pseudomonas.

A further problem associated with many commercially available cephalosporins is the lack of stability to $\beta$-lactamase enzyme producing organisms and the consequent loss of antibacterial activity. The compounds of the present invention exhibit good stability to $\beta$-lactamase enzymes and thus are particularly useful in treating organisms that are $\beta$-lactamase producers.

The cephalosporin derivatives referred to herein are generally names in accordance with the 'cephem' nomenclature and numbering system proposed in J.A.C.S. 1962, 84, 3400.

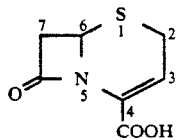

Accordingly the present invention provides a cephalosporin compound having a 3-position substituent of the formula (I):

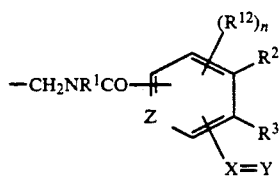

wherein:
R$^1$ is hydrogen, C$_{1-6}$ alkyl optionally substituted by any of halo, hydroxy, C$_{1-6}$ alkoxy, carboxy, amino, cyano, C$_{1-6}$ alkanoylamino, phenyl or heteroaryl, or R$^1$ is C$_{2-6}$ alkenyl;

R$^2$ is hydroxy or an in vivo hydrolysable ester thereof;

R$^3$ is hydroxy or an in vivo hydrolysable ester thereof;

Z is CH or N;

X is a group CR$^4$, wherein R$^4$ is hydrogen, optionally substituted C$_{1-6}$alkyl, aryl, arylC$_{1-6}$ alkyl, heteroaryl or heteroaryl C$_{1-6}$alkyl;

Y is a group NOR$^5$, NNR$^{51}$R$^6$, NR$^7$ (when —=Y is ortho to a hydroxy group) or CR$^8$R$^9$, wherein R$^5$ is hydrogen, optionally substituted C$_{1-6}$alkyl, arylC$_{1-6}$alkyl, heteroaryl C$_{1-6}$ alkyl, optionally substituted C$_{2-6}$ alkenyl, optionally substituted C$_{3-7}$ cycloalkyl, aryl or heteroaryl; R$^{51}$ is hydrogen, optionally substituted C$_{1-6}$alkyl, arylC$_{1-6}$alkyl, heteroarylC$_{1-6}$alkyl, optionally substituted C$_{2-6}$alkenyl, optionally substituted C$_{3-7}$cycloalkyl, aryl, heteroaryl, optionally substituted C$_{1-6}$alkanoyl, arylC$_{1-6}$alkanoyl, heteroarylC$_{1-6}$alkanoyl, optionally substituted C$_{2-6}$-alkenoyl, optionally substituted C$_{3-7}$cycloalkylcarbonyl, arylcarbonyl, heteroarylcarbonyl, carbamoyl, C$_{1-6}$alkylcarbamoyl, arylcarbamoyl or arylC$_{1-6}$alkylcarbamoyl; R$^6$ is hydrogen, C$_{1-6}$ alkyl or arylC$_{1-6}$alkyl; R$^7$ is optionally substituted C$_{1-6}$alkyl, arylC$_{1-6}$alkyl, heteroaryl C$_{1-6}$ alkyl, optionally substituted C$_{2-6}$ alkenyl, optionally substituted C$_{3-7}$ cycloalkyl, aryl or heteroaryl; R$^8$ and R$^9$ are independently halogen, hydrogen, optionally substituted C$_{1-6}$ alkyl, arylC$_{1-6}$alkyl, heteroarylC$_{1-6}$alkyl, optionally substituted C$_{2-6}$ alkenyl, C$_{3-7}$ cycloalkyl, aryl, heteroaryl, optionally substituted C$_{1-6}$ alkanoyl, optionally substituted C$_{1-6}$ alkoxycarbonyl, carboxy, arylcarbonyl, heteroarylcarbonyl or aryl C$_{1-6}$ alkoxycarbonyl;

or X=Y is a group —N=—R$^{10}$ or, when z is N, X=Y is also a group —N=CR$^{10}$R$^{11}$ wherein R$^{10}$ is optionally substituted aryl and R$^{11}$ is hydrogen or C$_{1-6}$alkyl;

R$^{12}$ is C$_{1-6}$alkyl, halo, hydroxy, hydroxy C$_{1-6}$alkyl, cyano, trifluoromethyl, nitro, amino, C$_{1-6}$alkylamino, di-C$_{1-6}$alkylamino, C$_{1-6}$alkanoyl, C$_{1-6}$alkoxy, C$_{1-6}$alkylthio, C$_{1-6}$alkanoyloxy, carbamoyl, C$_{1-6}$alkylcarbamoyl, di-C$_{1-6}$alkylcarbamoyl, carboxy, carboxy C$_{1-6}$alkyl, C$_{1-6}$alkoxycarbonylC$_{1-6}$alkyl, sulpho, sulphoC$_{1-6}$alkyl, C$_{1-6}$ alkanesulphonamido, C$_{1-6}$aalkoxycarbonyl, C$_{1-6}$alkanoylamino, thioureido or amidino, and n is zero to 2.

When used herein the term "heteroaryl" means a 5- or 6-membered ring containing 1 to 3 ring atoms selected from nitrogen, oxygen and sulphur and may be optionally substituted, for example by the substituents described hereinabove as values for R$^{12}$. Examples of heteroaryl include furanyl, pyridinyl, thiazolyl and isothiazolyl. Examples of aryl include phenyl and naphthyl, either of which may be optionally substituted, for example by the substituents described hereinabove as values for R$^{12}$.

In one aspect R$^1$ may be C$_{1-6}$ alkyl substituted by heteroaryl for example R$^1$ may be pyridinylmethyl or furanylmethyl. Particular meanings for R$^1$ are hydrogen, C$_{1-6}$ alkyl for example methyl, ethyl or propyl, hydroxy C$_{1-6}$alkyl for example 2-hydroxyethyl, halo C$_{1-6}$alkyl for example 2-chloroethyl or 2-fluoroethyl, C$_{1-6}$alkoxyC$_{1-6}$alkyl for example 2-methoxyethyl, 2-ethoxyethyl or methoxymethyl, carboxy C$_{1-6}$alkyl for example carboxymethyl, phenyl C$_{1-6}$alkyl for example benzyl or phenethyl, or C$_{2-6}$alkenyl for example allyl.

Preferably R$^1$ hydrogen, methyl or ethyl. Most preferably R$^1$ is hydrogen.

$R^2$ is hydroxy or an in vivo hydrolysable ester thereof. In vivo hydrolysable esters are those pharmaceutically acceptable esters that hydrolyse in the human or animal body to produce the parent hydroxy compound. Such esters can be identified by administering, e.g. intravenously to a test animal, the compound under test and subsequently examining the test animal's body fluids. Suitable in vivo hydrolysable esters include $C_{1-6}$ alkanoyloxy for example acetoxy, propionyloxy, pivaloyloxy, $C_{1-4}$alkoxycarbonyloxy for example ethoxycarbonyloxy, Phenylactoxy and phthalidyl.

$R^3$ is hydroxy or an in vivo hydrolysable ester thereof.

Conveniently both $R^2$ and $R^3$ have the same value and are both hydroxy or are both in vivo hydrolysable esters, for example they are both acetoxy or pivaloyloxy.

In one aspect X is a group $CR^4$.

In a particular aspect $R^4$ is $C_{1-6}$ alkyl (for example methyl, ethyl, n-propyl or n-butyl) optionally substituted. Suitable substituents include hydroxy, halo for example bromo, chloro or fluoro, $C_{1-6}$ alkoxy for example methoxy or ethoxy, amino, $C_{1-6}$ alkylamino for example methylamino or ethylamino, and di-$C_{1-6}$ alkylamino for example dimethylamino or diethylamino.

In another aspect $R^4$ is aryl for example phenyl or phenyl substituted by $C_{1-6}$ alkyl, or $R^4$ is heteroaryl for example furanyl, or $R^4$ is aryl $C_{1-6}$ alkyl for example benzyl or phenethyl, or $R^4$ is heteroaryl$C_{1-6}$alkyl for example pyridinyl methyl or furanylmethyl.

Particular meanings for $R^4$ are hydrogen, methyl, ethyl, n-propyl, n-butyl, phenyl, benzyl and furanyl.

Most favourably $R^4$ is hydrogen.

In one aspect Y is a group $NNR^{51}R^6$. In another aspect Y is a group $NR^7$ in which case the substituent —Y=Y is located in a position ortho to a hydroxy group on the benzene or pyridine ring of the formula (I). Generally such a hydroxy group will be one of $R^2$ and $R^3$.

In a preferred aspect Y is a group $NOR^5$ so forming an oxime.

$R^5$ is hydrogen, optionally substituted $C_{1-6}$ alkyl (for example methyl, ethyl, n-propyl, isopropyl or n-butyl), aryl$C_{1-6}$alkyl (for example benzyl or phenethyl), heteroaryl$C_{1-6}$alkyl (for example furanylmethyl), optionally substituted $C_{2-6}$ alkenyl (for example allyl), optionally substituted $C_{3-7}$ cycloalkyl (for example cyclobutyl, cyclopentyl, or cyclohexyl), aryl (for example phenyl or naphthyl) or heteroaryl (for example pyridinyl, furanyl or imidazolyl). Suitable optional substituents for alkyl, cycloalkyl and alkenyl include hydroxy, $C_{1-6}$ alkoxy for example methoxy and ethoxy, halo for example bromo, chloro or fluoro, carboxy, $C_{1-4}$alkylcarbamoyl for example methylcarbamoyl, di-$C_{1-4}$alkylcarbamoyl for example dimethylcarbamoyl, $C_{1-6}$alkylthio for example methylthio, amino, $C_{1-6}$alkylamino for example methylamino and ethylamino, di$C_{1-6}$alkylamino for example dimethylamino and diethylamino, cyano, $C_{1-6}$alkanesulphonamido for example methanesulphonamido, $C_{1-6}$alkoxycarbonyl for example methoxycarbonyl and ethoxycarbonyl or $C_{1-6}$alkanoyl.

Particular meanings for $OR^5$ include hydroxy, methoxy, ethoxy, n-propoxy, isopropoxy, t-butoxy, cyclopropoxy, cyclobutoxy, cyclopentoxy, allyloxy, 2-chloroethoxy, 2-fluoroethoxy, 2-bromoethoxy, 2-hydroxyethoxy, 3-hydroxypropxy, 2-methoxyethoxy, 2-ethoxyethoxy, 2-methylthioethoxy, 2-aminoethoxy, 3-aminopropoxy, 2-methylaminoethoxy, 2-dimethylaminoethoxy, cyanomethoxy, 2-cyanoethoxy, carboxymethoxy, 2-carboxyethoxy, 1-carboxyethoxy, 1-carboxycyclobutoxy, 1-carboxycyclopentoxy, 2-carboxyprop-2-oxy, methoxycarbonylmethoxy, ethoxycarbonylmethoxy, acetoxy and benzyloxy.

$R^{51}$ is hydrogen, optionally substituted $C_{1-6}$ alkyl (for example methyl, ethyl, n-propyl, isopropyl or n-butyl), aryl$C_{1-6}$alkyl (for example benzyl or phenethyl), heteroaryl$C_{1-6}$alkyl (for example furanylmethyl), optionally substituted $C_{2-6}$ alkenyl (for example allyl), optionally substituted $C_{3-7}$ cycloalkyl (for example cyclobutyl, cyclopentyl, or cyclohexyl), aryl (for example phenyl or naphthyl), heteroaryl (for example pyridinyl, furanyl or imidazolyl), $C_{1-6}$alkanoyl (for example formyl, acetyl or propionyl), aryl$C_{1-6}$ alkanoyl (for example phenylacetyl), heteroaryl$C_{1-6}$alkanoyl (for example furanylacetyl), optionally substituted $C_{2-6}$alkenoyl (for example propenecarbonyl), optionally substituted $C_{3-7}$ cycloalkylcarbonyl (for example cyclopentylcarbonyl), arylcarbonyl (for example benzoyl), heteroarylcarbonyl (for example furancarbonyl), carbamoyl, $C_{1-6}$alkylcarbamoyl (for example methylcarbamoyl), arylcarbamoyl (for example phenylcarbamoyl) and aryl$C_{1-6}$ alkylcarbamoyl (for example benzylcarbamoyl). Suitable optional substituents for alkyl, cycloalkyl and alkenyl include hydroxy, $C_{1-6}$ alkoxy for example methoxy and ethoxy, halo for example bromo, chloro or fluoro, carboxy, $C_{1-4}$alkylcarbamoyl for example methylcarbamoyl, di-$C_{1-4}$alkylcarbamoyl for example dimethylcarbamoyl, $C_{1-6}$alkylthio for example methylthio, amino, $C_{1-6}$alkylamino for example methylamino and ethylamino, di-$C_{1-6}$alkylamino for example dimethylamino and diethylamino, cyano, $C_{1-6}$alkanesulphonamido for example methanesulphonamido, $C_{1-6}$alkoxycarbonyl for example methoxycarbonyl and ethoxycarbonyl or $C_{1-6}$alkanoyl.

$R^6$ is hydrogen, $C_{1-6}$ alkyl for example methyl, ethyl or n-propyl, or aryl$C_{1-6}$alkyl for example benzyl or phenethyl.

Particular meanings for —$NR^{51}R^6$ include anilino, optionally substituted anilino, benzoylamino, phenylacetamindo, ureido, methylureido and $N^1$-benzylureido (—N(CONH$_2$)CH$_2$Ph).

$R^7$ is optionally substituted $C_{1-6}$ alkyl (for example methyl, ethyl, n-propyl, isopropyl or n-butyl), aryl$C_{1-6}$alkyl (for example benzyl or phenethyl), heteroaryl$C_{1-6}$alkyl (for example furanylmethyl), optionally substituted $C_{2-6}$ alkenyl (for example allyl), $C_{3-7}$ cycloalkyl (for example cyclobutyl, cyclopentyl, or cyclohexyl), aryl (for example phenyl or haphthyl) or heteroaryl (for example pyridinyl, furanyl or imidazolyl). Suitable optional substituents for alkyl and alkenyl include hydroxy, $C_{1-6}$ alkoxy for example methoxy and ethoxy, halo for example bromo, chloro or fluoro, carboxy, $C_{1-4}$alkylcarbamoyl for example methylcarbamoyl, di-$C_{1-4}$alkylcarbamoyl for example dimethylcarbamoyl, $C_{1-6}$alkylthio for example methylthio, amino, $C_{1-6}$ alkylamino for example methylamino and ethylamino, di-$C_{1-6}$alkylamino for example dimethylamino and diethylamino, cyano, $C_{1-6}$ alkanesulphonamido for example methanesulphonamido, $C_{1-6}$ alkoxycarbonyl for example methoxycarbonyl and ethoxycarbonyl or $C_{1-6}$ alkanoyl.

In another preferred aspect Y is a group $CR^8R^9$. $R^8$ and $R^9$ are independently halogen (for example chloro, bromo or fluoro), hydrogen, optionally substituted $C_{1-6}$ alkyl (for example methyl, ethyl, n-propyl, isopropyl or n-butyl), aryl$C_{1-6}$alkyl (for example benzyl or phenethyl), heteroarylC$_{1-6}$alkyl (for example furanylmethyl), optionally substituted C$_{2-6}$ alkenyl (for example allyl), C$_{3-7}$ cycloalkyl (for example cyclobutyl, cyclopentyl, or cyclohexyl), aryl (for example phenyl or naphthyl), heteroaryl (for example pyridinyl, furanyl or imidazolyl), optionally substituted C$_{1-6}$ alkoxycarbonyl (for example methoxycarbonyl or ethoxycarbonyl), carboxy, arylcarbonyl (for example benzoyl), heteroarylcarbonyl (for example furanoyl or pyridinecarbonyl), optionally substituted C$_{1-6}$ alkanoyl (for example acetyl or propionyl) or aryl C$_{1-6}$ alkoxycarbonyl (for example benzoxycarbonyl). Suitable optional substituents for alkyl, alkenyl, alkoxycarbonyl, alkanoyl and any aryl or heteroaryl group include hydroxy, C$_{1-6}$ alkoxy for example methoxy and ethoxy, halo for example bromo, chloro or fluoro, carboxy, C$_{1-4}$alkyl carbamoyl for example methylcarbamoyl, di-C$_{1-4}$alkylcarbamoyl for example dimethylcarbamoyl, C$_{1-6}$alkylthio for example methylthio, amino, C$_{1-6}$alkylamino for example methylamino and ethylamino, di-C$_{1-6}$alkylamino for example dimethylamino and diethylamino, cyano, C$_{1-6}$alkanesulphonamido for example methanesulphonamido, C$_{1-6}$alkoxycarbonyl for example methoxycarbonyl and ethoxycarbonyl or C$_{1-6}$alkanoyl.

Particular meanings for R$^8$ and R$^9$ include hydrogen, methyl, ethyl, phenyl, acetyl, methoxycarbonyl and pyridinyl.

In another aspect the group —X=Y is —N=NR$^{10}$ or, when Z is N, X=Y may also be —N=CR$^{10}$R$^{11}$. R$^{10}$ is aryl (for example phenyl or naphthyl) and optional substituents include hydroxy, C$_{1-6}$ alkoxy (for example methoxy or ethoxy), cyano, nitro, halo (for example chloro, bromo or fluoro), C$_{1-6}$alkyl (for example methyl) and C$_{1-6}$alkylthio (for example methylthio). R$^{11}$ is hydrogen or C$_{1-6}$ alkyl (for example methyl or ethyl).

Preferably —X=Y is a group —N=NR$^{10}$ for example phenylazo or 2,4,6-trimethylphenylazo.

Particular values for R$^{12}$ are C$_{1-6}$alkyl for example methyl or ethyl, halo for example chloro, fluoro or bromo, hydroxy, hydroxyC$_{1-6}$alkyl for example hydroxyethyl, cyano, amino, C$_{1-6}$alkylamino for example methylamino or ethylamino, di-C$_{1-6}$alkyl amino for example dimethylamino or diethylamino, C$_{1-6}$alkoxy for example methoxy or ethoxy, carboxyC$_{1-6}$alkyl for example carboxymethyl, C$_{1-6}$alkanoylamino for example acetamido, trifluoromethyl, carboxy, carbamoyl, C$_{1-6}$alkylcarbamoyl for example methylcarbamoyl, diC$_{1-6}$alkylcarbamoyl for example dimethylcarbamoyl, C$_{1-6}$alkanoyl for example acetyl, C$_{1-6}$alkylthio for example methylthio, C$_{1-6}$ alkanoyloxy for example acetoxy, C$_{1-6}$ alkoxycarbonyl for example methoxycarbonyl or ethoxycarbonyl and C$_{1-6}$ alkoxycarbonylC$_{1-6}$alkyl for example methoxycarbonylmethyl.

Of these, favoured substituents are bromo, chloro, fluoro, nitro, cyano and hydroxy. Preferably n is zero or one.

It will be realised, of course, that the present invention covers all isomeric and tautomeric forms of the aforementioned compounds. In particular most groups —X=Y may exist in cis- or trans form or in E- or Z-configuration, as appropriate. The present invention also covers mixtures of such isomers.

A favoured class of cephalosporin compounds of the present invention has a 3-position substituent of the formula (II):

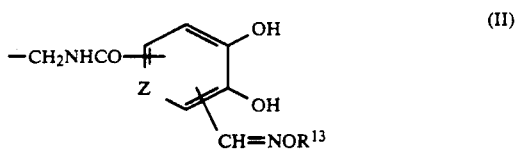

wherein Z is as hereinbefore defined and R$^{13}$ is hydrogen, C$_{1-6}$alkyl, benzyl, carboxyC$_{1-6}$alkyl or allyl. In particular R$^{13}$ is hydrogen, methyl, ethyl, carboxymethyl, allyl or benzyl. In particular Z is —CH=.

A further favoured class of cephalosporin compounds of the present invention is that of the formula (IIa):

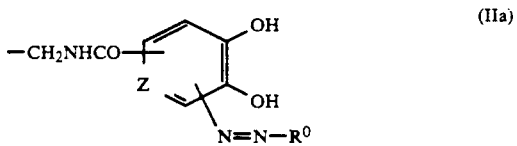

wherein Z is as hereinbefore defined and R$^0$ is phenyl or 2,4,6-trimethylphenol. In particular Z is —N=.

As stated hereinbefore the present invention relates to cephalosporins having a novel 3-position substituent. A particular class of cephalosporins within the present invention is that of the formula (III):

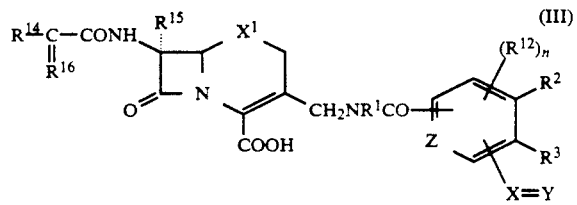

and salts and esters thereof wherein R$^1$-R$^3$, Z, n, X, Y and R$^{12}$ are as hereinbefore defined;

X$^1$ is sulphur, oxygen, methylene or sulphinyl;

R$^{15}$ is hydrogen, methoxy or formamido; and

R$^{14}$ and R$^{16}$ are groups known for such positions in the cephalosporin art.

Preferably X$^1$ is sulphur.

Preferably R$^{15}$ is hydrogen.

R$^{14}$ is for example 2-aminothiazol-4-yl or 2-aminooxazol-4-yl each optionally substituted in the 5-position by fluorine, chlorine or bromine, or R$^{14}$ is 5-aminoisothiazol-3-yl, 5-amino-1,2,4-thiadiazol3-yl, 3-aminopyrazol-5-yl, 3-aminopyrazol-4-yl, 2-aminopyrimidin-5-yl, 2-aminopyrid-6-yl, 4-aminopyrimidin-2-yl, 2-amino-1,3,4-thiadiazol-5-yl or 5-amino-1-methyl-1,2,4-triazol-3-yl;

R$^{16}$ is for example of the formula =N.O.R$^{17}$ (having the syn configuration about the double bond) wherein R$^{17}$ is hydrogen, (1-6C)alkyl, (3-8C)cycloalkyl, (1-3C)alkyl(3-6C)cycloalkyl, (3-6C)cycloalkyl(1-3C)alkyl, (3-6C)alkenyl, optionally substituted by carboxy, (5-8C)cycloalkenyl, (3-6C)alkynyl, (2-5C)alkylcarbamoyl, phenylcarbamoyl, benzylcarbamoyl, (1-4C)alkylcarbamoyl(1-4C)alkyl, di(1-4C)alkylcarbamoyl(1-4C)alkyl, (1-4C)haloalkylcarbamoyl(1-4C)alkyl, (1-3C)haloalkyl, (2-6C)hydroxyalkyl, (1-4C)alkoxy(2-4C)alkyl, (1-4C)alkylthio(2-4C)alkyl, (1-4C)alkanesulphinyl(1-4C)alkyl, (1-4C)alkanesulphonyl(1-4C)alkyl, (2-6C)aminoalkyl, (1-4C)alkylamino(1-5C)alkyl, (2-8C)dialkylamino(2-

6C)alkyl, (1-5C)cyanoalkyl, 3-amino-3-carboxypropyl, 2-(amidinothio)ethyl, 2-(N-aminoamidinothio)ethyl, tetrahydropyran-2-yl, thietan-3-yl, 2-oxopyrrolidinyl, or 2-oxotetrahydrofuranyl, or $R^{17}$ is of the formula IV:

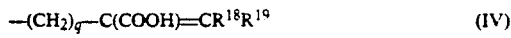

$$-(CH_2)_q-C(COOH)=CR^{18}R^{19} \qquad (IV)$$

wherein q is one or two and $R^{18}$ and $R^{19}$ are independently hydrogen or $C_{1-4}$alkyl; or $R^{17}$ is of the formula V:

$$-CR^{20}R^{21}-(CH_2)_r-COR^{22} \qquad (V)$$

wherein r is 0-3, $R^{20}$ is hydrogen, (1-3C)alkyl or methylthio, $R^{21}$ is hydrogen, (1-3C)alkyl, (3-7C)cycloalkyl, cyano, carboxy, (2-5C)carboxyalkyl or methanesulphonylamino, or $R^{20}$ and $R^{21}$ are joined to form, together with the carbon to which they are attached, a (3-7C)carbocyclic ring, and $R^{22}$ is hydroxy, amino, (1-4C)alkoxy, (1-4C) alkylamino or of the formula $NHOR^{23}$ in which $R^{23}$ is hydrogen or (1-4C)alkyl;

or $R^{16}$ may be of the formula $-CH.R^{24}$ wherein $R^{24}$ is hydrogen, halogen, (1-6C)alkyl, (3-7C)cycloalkyl, (2-6C)alkenyl, (3-7C)cycloalkenyl, phenyl or benzyl.

Particular meanings for $R^{17}$ are hydrogen, methyl, ethyl, isopropyl, t-butyl, cyclopropyl, cyclobutyl, cyclopentyl, cyclohexyl, methylcyclopropyl, methylcyclobutyl, methylcyclopentyl, methylcyclohexyl, cyclopropylmethyl, cyclobutylmethyl, cyclopentylmethyl, allyl, cyclopentenyl, cyclohexenyl, propargyl, methylcarbamoyl, ethylcarbamoyl, phenylcarbamoyl, benzylcarbamoyl, 2-chloroethyl, 2-fluoroethyl, 2-bromoethyl, 2-hydroxyethyl, 3-hydroxypropyl, 2-methoxyethyl, 2-ethoxyethyl, 2-methylthioethyl, 2-methanesulphinylethyl, 2-methanesulphonylethyl, 2-aminoethyl, 3-aminopropyl, 2-methylaminoethyl, 2-dimethylaminoethyl, cyanomethyl, 2-cyanoethyl, azidomethyl, 2-azidoethyl, ureidomethyl, 3-amino-3-carboxypropyl, 2-(amidino)ethyl, 2-(N-aminoamidino)-ethyl, tetrahydropyran-2-yl, thietan-3-yl, 2-oxopyrrolidinyl and 2oxotetrahydrofuran-3-yl, or, when $R^{17}$ is of the formula IV in which q is 1 or 2, a particular meaning for $R^{17}$ is when $R^{18}$ and $r^{19}$ are hydrogen or methyl, or, when $R^{17}$ is of the formula V a particular meaning for $R^{17}$ is when r=0 and $R^{20}$ is hydrogen, methyl or methylthio, $R^{21}$ is hydrogen, methyl, cyclopropyl, cyclobutyl, cyclopentyl, cyclohexyl, cyano, carboxy, carboxymethyl, 2-carboxyethyl or methanesulphonylamino, or when $R^{19}$ and $R^{21}$ are joined to form, together with the carbon to which they are attached, a cyclopropane, cyclobutane, cyclopentane, cyclohexane or cycloheptane ring and $R^{22}$ is hydroxy, amino, methoxy, ethoxy, methylamino, ethylamino, or of the formula $NHOR^{23}$ in which $R^{23}$ is hydrogen, methyl or ethyl.

Preferably $R^{17}$ is $C_{1-6}$alkyl for example methyl or ethyl, 1-carboxycyclobutyl, 1-carboxycyclopentyl, or 2-carboxyprop-2-yl. In particular $R^{17}$ is 2-carboxyprop-2-yl.

Particular meanings for $R^{24}$ are hydrogen, methyl, ethyl or chlorine.

A particularly preferred class of cephalosporins of the present invention is that wherein $R^{14}$ is 2-aminothiazol-4-yl, $R^{16}$ is a group $=NOR^{17}$ wherein $R^{17}$ is $C_{1-6}$alkyl, 1-carboxycyclobutyl, 1-carboxycyclopentyl or 2-carboxyprop-2-yl, $R^{15}$ is hydrogen, $X^1$ is sulphur and the 3-position substituent is of the formula (II) or (IIa).

As stated hereinbefore the compounds of this invention are primarily intended for use in therapy. Therefore in a preferred aspect the present invention provides a cephalosporin compound having a 3-position substituent of the formula I or a pharmaceutically acceptable salt or ester thereof. Suitable salts include acid addition salts such as hydrochloride, hydrobromide, citrate, maleate and salts formed with phosphoric and sulphuric acid. In another aspect suitable salts are base salts such as an alkali metal salt for example sodium or potassium, an alkaline earth metal salt for example calcium or magnesium, an organic amine salt for example triethylamine, morpholine, N-methylpiperidine, N-ethylpiperidine, procaine, dibenzylamine, or N,N-dibenzylethylamine.

In order to use a compound of the present invention or a pharmaceutically acceptable salt or ester thereof for the therapeutic treatment of mammals including humans, in particular in treating infection, it is normally formulated in accordance with standard pharmaceutical practice as a pharmaceutical composition.

Therefore in another aspect the present invention provides a pharmaceutical composition which comprises a cephalosporin compound having a 3-position substituent of the formula I or a pharmaceutically acceptable salt or ester thereof and a pharmaceutically acceptable carrier.

The pharmaceutical compositions of this invention may be administered in standard manner for the disease condition that it is desired to treat, for example by oral, rectal or parenteral administration. For these purposes it may be formulated by means known to the art into the form of, for example, tablets, capsules, aqueous or oily solutions or suspensions, emulsions, dispersible powders, suppositories and sterile injectable aqueous or oily solutions or suspensions.

In addition to the pharmaceutically acceptable cephalosporin derivative of the present invention the pharmaceutical composition of the invention may also contain, or be co-administered with, one or more known drugs selected from other clinically useful antibacterial agents (for example other beta-lactams or aminoglycosides), inhibitors of beta-lactamase (for example clavulanic acid), renal tubular blocking agents (e.g. probenicid) and inhibitors of metabolising enzymes (for example inhibitors of peptidases, for example Z-2-acylamino-3-substitute propenoates).

A preferred pharmaceutical composition of the invention is one suitable for intravenous, subcutaneous or intramuscular injection, for example a sterile injectable containing between 1 and 50% w/w of the cephalosporin derivative, or one suitable for oral administration in unit dosage form, for example a tablet or capsule which contains between 100 mg. and 1 g. of the cephalosporin derivative.

The pharmaceutical compositions of the invention will normally be administered to man in order to combat infections caused by bacteria, in the same general manner as that employed for cephalothin, cefoxitin, cephradine, ceftazidime and other known clinically used cephalosporin derivatives, due allowance being made in terms of dose levels for the potency of the cephalosporin derivative of the present invention relative to the known clinically used cephalosporins. Thus each patient will receive a daily intravenous, subcutaneous or intramuscular dose of 0.05 to 30 g., and preferably 0.1 to 10 g., of the cephalosporin derivative, the composition being administered 1 to 4 times per day, preferably 1 or 2 times a day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose. Thus a preferred daily oral dose is 0.5 to 10 g. of the cephalosporin derivative, the composition being administered 1 to 4 times per day.

In a further aspect the present invention provides a process for preparing a cephalosporin compound having a 3-position substituent of the formula (I), which process comprises:

(a) reacting a cephalosporin compound having a 3-position substituent of the formula: —CH$_2$NHR$^1$ wherein R$^1$ is as hereinbefore defined with a compound of the formula (VI):

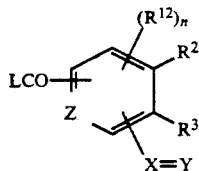

wherein R$^2$, R$^3$, X, Y, R$^{12}$ and n are as hereinbefore defined and L is a leaving group; or b) for compounds of the formula (II), reacting a compound of the formula (VII) with a compound of the formula (VIII) or a reactive derivative thereof:

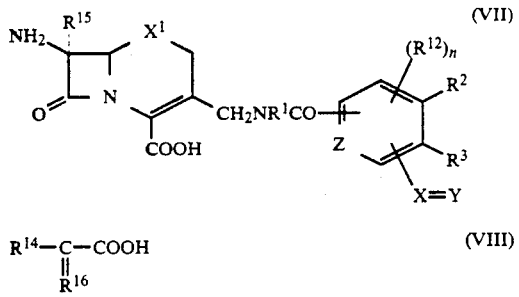

wherein R$^1$-R$^3$, R$^{12}$, R$^{14}$-R$^{16}$, n, X, X$^1$ and Y are as hereinbefore defined; or c) for compounds of the formula (III) wherein R$^{16}$ is a group =NOR$^{17}$, reacting a compound of the formula (IX):

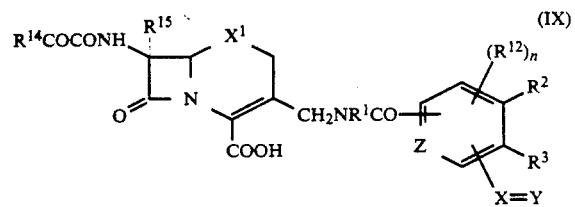

wherein R$^1$-R$^3$, R$^{12}$, R$^{14}$, R$^{15}$, X$^1$, X, Y and n are as hereinbefore defined, with a compound of the formula: R$^{17}$ONH$_2$ wherein R$^{17}$ is as hereinbefore defined; or d) for compounds of the formula (III) wherein R$^{16}$ is a group =NOR$^{17}$ and R$^{17}$ is other than hydrogen, reacting a compound of the formula (III) as hereinbefore defined wherein R$^{16}$ is a group =NOH with compound of the formula (X):

$$L^1—R^{25} \qquad (X)$$

wherein L$^1$ is a leaving group and R$^{25}$ is a group R$^{17}$ other than hydrogen; or e) for compounds of the formula (III) forming a group R$^{15}$ by cyclising an appropriate precursor thereof:

wherein any functional groups are optionally protected: and thereafter, if necessary:

i) removing any protecting group,
ii) for preparing in vivo hydrolysable esters, esterifying corresponding hydroxy groups,
iii) converting compounds wherein X$^1$ is S to compounds wherein X$^1$ is sulphinyl and vice versa,
iv) forming a pharmaceutically acceptable salt.

In the reaction between a cephalosporin compound having a 3-position substituent of the formula —CH$_2$NHR$^1$, and a compound of the formula (VI), conveniently L is a leaving group such as halo for example chloro, bromo or iodo. Most suitably the reaction is performed under conditions conventional for the reaction of acid halides with amines for example in the presence of an organic amine such as triethylamine. Suitably the reaction is performed at an ambient or lower temperature in a substantially inert solvent such as dimethylformamide and/or dichloromethane. In an alternative aspect the leaving group L is part of an activated ester formed with the acid precursor of the compound of the formula VI, i.e. a compound wherein L is —OH provides an activated ester, e.g. dicyclohexylcarbodi-imide provides an activated ester of the formula VI wherein L is —OC(NHC$_6$H$_{11}$)=NC$_6$H$_{11}$, which group is displaced by the cephalosporin having a 3-position substituent of the formula: —CH$_2$NHR$^1$. Formation and reaction of the active ester is performed in conventional manner in the presence of reaction promotors such as hydroxybenzotriazole and triethylamine, for example in a substantially inert organic solvent such as dimethylformamide at a non-extreme temperature such as 10° C. -50° C.

The cephalosporin starting-materials for this reaction are known from the art, or are made by methods analogous to those of the art. See for example EP-A-127992 and EP-A-164944.

The compounds of the formula VI are either known in the art or are made by methods analogous thereto. For example compounds wherein L is chloro are conveniently prepared from the corresponding acids. The acids are known or are prepared by methods known to those skilled in the art, for example as in the hereinafter described Examples. In particular the group —CR$^4$=CR$^8$R$^9$ may be formed by the reaction of an appropriate aldehyde or ketone with a Wittig reagent, optionally using the Horner modification. Alternatively groups —CR$^4$=CR$^8$R$^9$, in particular where one or both of R$^8$ and R$^9$ is electron-withdrawing, can be formed by a standard aldol condensation or reaction of an appropriate aldehyde or ketone with an activated methylene group (e.g. Knoevenagel condensation). A further method of forming certain groups —CH=CR$^8$R$^9$ is to react a aldehyde in the Perkin condensation. The above methods of forming carbon-carbon double bonds are illustrative only and the skilled man will be aware of alternative methods. The groups —CR$^4$=NOR$^5$, —CR$^4$=NNR$^{51}$R$^6$ and —CR$^4$=NR$^7$ can, for example, be formed in standard manner by reacting an appropriate aldehyde or ketone with a hydroxylamine derivative, an appropriate hydrazine, acyl hydrazine, semicarbazine (NH₂NR'CONHR'') or an appropriate amine. The groups —N=NR¹⁰ and —N=CR¹⁰R¹¹ can, for example, be formed in standard manner by diazotisation or by reaction of an amine with an appropriate aldehyde or ketone.

The reaction between compounds of the formulae VII and VIII is performed under conditions conventional in the cephalosporin art, for example under standard acylation conditions wherein for example the acid is activated as an acid bromide, acid chloride, anhydride or activated ester, or the reaction is performed in the presence of a coupling reagent such as dicyclohexylcarbodi-imide.

The compounds of the formula VII can be prepared in a manner analogous to that described for the compounds having the 3-substituent of the formula I, with the 7-amino group being optionally protected.

The reaction between compounds of the formula IX and R¹⁷ONH₂ is performed under conditions standard in the general chemical and/or cephalosporin art. The compounds of the formula IX can be prepared in a manner analogous to that described for the compounds having the 3-substituent of the formula I.

The reaction between the compound of the formula III wherein R¹⁶ is a group =NOH and a compound of the formula X is performed under conditions standard in the general chemical and/or cephalosporin art.

A group R¹⁴ may be formed by cyclizing an appropriate precursor. For example compounds of the formulae XI and XII:

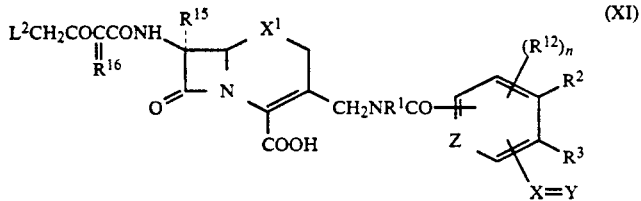

NH₂CSNH₂ (XII)

wherein R¹-R³, R¹², R¹⁵, r¹⁶, X¹, X, Y and n are as hereinbefore defined and L² is a leaving group, may be reacted to form a 2-aminothiazol-4-yl group. A nitrogen atom of the thiourea may be optionally protected during this cyclization.

The compounds of the formula XI can be prepared in a manner analogous to that described for the compounds having a 3-substituent of the formula I.

The compounds of the formulae VIII, X and R¹⁷ONH₂ are known from, or can be made by the methods of, the general chemical and/or cephalosporin art.

The compounds of the formulae VII, IX and XI are novel and as such form a further aspect of the present invention.

In the process of this invention any functional group can be optionally protected, if appropriate. Such protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxyl protecting group may be the residue of an ester-forming aliphatic or araliphatic alcohol or of an ester-forming phenol, silanol or stannanol (the said alcohol, phenol, silanol or stannanol preferably containing 1–20 carbon atoms).

Examples of carboxyl protecting groups include straight or branched chain (1-12C)alkyl groups (e.g. isopropyl, t-butyl); halo lower alkyl groups (e.g. 2-iodoethyl, 2,2,2-trichloroethyl); lower alkoxy lower alkyl groups (e.g. methoxymethyl, ethoxymethyl, isobutoxymethyl); lower aliphatic acyloxy lower alkyl groups, (e.g. acetoxymethyl, propionyloxymethyl, butyryloxymethyl, pivaloyloxymethyl); lower alkoxycarbonyloxy lower alkyl groups (e.g. 1-methoxy-carbonyloxyethyl, 1-ethoxycarbonyloxyethyl); aryl lower alkyl groups (e.g. p-methoxybenzyl, o-nitrobenzyl, p-nitrobenzyl, benzhydryl and phthalidyl); tri(lower alkyl)silyl groups (e.g. trimethylsilyl and t-butyldimethylsilyl); tri(lower alkyl)silyl lower alkyl groups (e.g. trimethylsilylethyl); and (2-6C) alkenyl groups (e.g. allyl and vinylethyl).

Methods particularly appropriate for the removal of carboxyl protecting groups include for example acid-, base-, metal- or enzymically-catalyzed hydrolysis.

Examples of hydroxyl protecting groups include lower alkanoyl groups (e.g. acetyl); lower alkoxycarbonyl groups (e.g. t-butoxycarbonyl); halo lower alkoxycarbonyl groups (e.g. 2-iodoethoxycarbonyl, 2,2,2-trichloroethoxycarbonyl); aryl lower alkoxycarbonyl groups (e.g. benzoyloxycarbonyl, p-methoxybenzyloxycarbonyl, o-nitrobenzyloxycarbonyl, p-nitrobenzyloxycarbonyl); tri lower alkylsilyl (e.g. trimethylsilyl, t-butyldimethylsilyl) and aryl lower alkyl (e.g. benzyl) groups. In addition two hydroxy groups substituted on adjacent carbon atoms, for example in the catechol moiety, may be protected in the form of a cyclic acetal such as the methylenedioxy moiety.

Examples of amino protecting groups include formyl, aralkyl groups (e.g. benzyl and substituted benzyl, e.g. p-methoxybenzyl, nitrobenzyl and 2,4-dimethoxybenzyl, and triphenylmethyl); di-p-anisylmethyl and furylmethyl groups; acyl (e.g. alkoxycarbonyl and aralkoxycarbonyl e.g. t-butoxycarbonyl and benzyloxycarbonyl); trialkylsilyl (e.g. trimethylsilyl and t-butyldimethylsilyl); alkylidene (e.g. methylidene); benzylidene and substituted benzylidene groups; and the phthalimido group.

The following biological test methods, data and Examples serve to illustrate this invention.

Antibacterial Activity

The pharmaceutically acceptable cephalosporin compounds of the present invention are useful antibacterial agents having a broad spectrum of activity in vitro against standard laboratory microorganisms, both Gram-negative and Gram-positive, which are used to screen for activity against pathogenic bacteria. The antibacterial spectrum and potency of a particular compound may be determined in a standard test system. In particular the cephalosporins of the present invention show good stability to 62-lactamase enzymes and have particularly high activity in vitro against strains of *Pseudomonas aeruginosa* and other Gram-negative aerobic bacteria.

The antibacterial properties of the compounds of the invention may also be demonstrated in vivo in conventional mouse protection tests.

Cephalosporin derivatives have generally been found to be relatively non-toxic to warm-blooded animals, and this generalisation holds true for the compounds of the present invention. Compounds representative of the present invention were administered to mice at doses in excess of those required to afford protection against bacterial infections, and no overt toxic symptoms or side effects attributable to the administered compounds were noted.

The following results were obtained for representative compounds on a standard in vitro test system using Isosensitest agar medium. The antibacterial activity is described in terms of the minimum inhibitory concentration (M1C) determined by the agar-dilution technique with an inoculum size of $10^4$ CFU/spot.

| ORGANISM | MIC (µl/ml) EXAMPLE | | | | | | |
|---|---|---|---|---|---|---|---|
| | 2 | 3 | 4 | 6 | 7 | 9 | 12 |
| P. aeruginosa | 0.06 | 0.06 | 0.008 | 0.06 | 0.03 | 0.125 | 0.03 |

| ORGANISM | MIC (µl/ml) EXAMPLE | | | | | | |
|---|---|---|---|---|---|---|---|
| | 2 | 3 | 4 | 6 | 7 | 9 | 12 |
| PU21 (A8101028) Ent. cloacae | 0.25 | 0.06 | 0.125 | 0.125 | 0.25 | 0.5 | 0.03 |
| P99 (A8401054) Serr. marcesens | 0.03 | 0.015 | 0.008 | 0.03 | 0.03 | 0.06 | 0.008 |
| (A8421003) Pr. morganii | 0.03 | 0.015 | 0.03 | 0.06 | 0.06 | 0.125 | 0.015 |
| (A8433001) Kleb. aerogenes | 0.015 | 0.008 | 0.008 | 0.03 | 0.03 | 0.03 | 0.008 |
| (A8391027) E. coli | 0.008 | 0.008 | 0.008 | 0.008 | 0.008 | 0.008 | 0.008 |
| DCO (A8341098) St. aureus | 16 | 16 | 32 | 8 | 16 | 64 | 32 |
| 147N (A8601052) S. dublin | 0.03 | 0.015 | 0.008 | 0.125 | 0.03 | 0.06 | 0.008 |
| (A8369001) Strep. pyogenes (A681018) | 0.125 | 0.25 | 0.25 | 1 | 0.25 | 0.25 | NA |

EXAMPLES 1-12

To a suspension of the appropriate 3-aminomethyl cephalosporin (1 mM) in dimethylformamide (10 ml), at 0° C., was added triethylamine (3 mM) followed by the appropriate activated ester (1.1 mM) in dimethylformamide (5 ml). The reaction mixture was stirred at 0° C. for 30 minutes and subsequently at room temperature for 4 hours. The mixture was concentrated to about 2.5 ml under reduced pressure and the residue diluted with ice-cold water (50 ml) to give a precipitate which was collected by filtration and purified on Diaion HP2OSS resin using acetonitrile/0.2% aqueous trifluoroacetic acid in gradient elution (increasing acetonitrile). Evaporation and freezedrying of the appropriate fractions gave the desired product.

The following general procedure was used for preparing the activated ester used in the above reaction: To the appropriate benzoic acid (1.5 mM) and N-hydroxy succinimide (1.65 mM) in dimethylformamide (4 ml) and dichloromethane (4 ml) was added dicyclohexylcarbodi-imide (1.65 mM) over about 3 minutes. The reaction mixture was stirred for 3-4 hours at 20° C., filtered to remove dicyclohexyl urea and the filtrate concentrated to about 5 ml volume. This solution was used directly without further purification.

TABLE 1

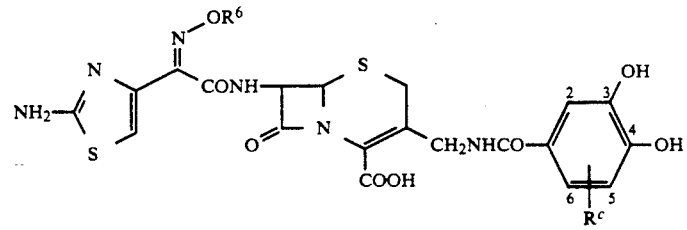

| Example | $R^b$ | $R^c$ | Footnotes |
|---|---|---|---|
| 1 | C(CH₃)₂COOH | 5-CH=N—OH | |
| 2 | " | 5-CH=N—OCH₃ | 1 |
| 3 | " | 5-CH=N—OCH₂Ph | |
| 4 | " | 5-CH=N—OCH₂COOH | 2 |
| 5 | CH₂CH₃ | 5-CH=N—OCH₂COOH | 2 |
| 6 | C(CH₃)₂COOH | 5-CH=CHPh(trans-isomer) | |
| 7 | " | 5-CH=N—NHPh | |
| 8 | " | 6-CH=N—OCH₂Ph | |
| 9 | " | 6-CH=N—OCH₂CH=CH₂ | |
| 10 | " | 6-CH=N—OCH₂Ph(2,6-di-Cl₂) | |
| 11 | " | 6-CH=N—OCH₂CH₂CH₂CH₃) | |

TABLE 1-continued

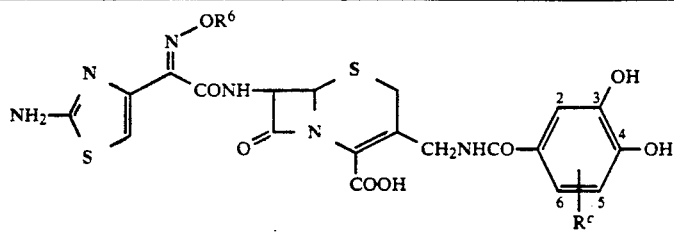

| Example | R$^b$ | R$^c$ | Footnotes |
|---------|-------|-------|-----------|
| 12 | " | 5-CH=N—N(CONH$_2$)CH$_2$Ph | |

Footnotes
1. This compound was also prepared from its diacetoxy derivative:
To a suspension of the appropriate 3-aminomethyl cephalosporin (1 mM) in dimethylformamide (10 ml) at 5–10° C. was added, N-methyl morpholine (2 mM) in dichloromethane (5 ml) (followed by 3,4-diacetoxy-5-(l-methoxyimino)benzoyl chloride).
The reaction mixture was stirred for 2 hours at 20° C. and then concentrated. The reaction mixture was diluted with water at 0° C. and the pH adjusted with 2N HCl to 3.5. The precipitate thus obtained was filtered off and stirred with a dilute solution of ammonia at pH 9.0 for 2 hours to cleave the protecting groups. The product was purified according to the general procedure.
The carbonyl chloride was prepared from the corresponding acid by treatment with 1 equivalent of PCl$_5$ and refluxing for 1 hour. 3,4-Diacetoxy 5-(1-methoxyimino)benzoic acid was prepared from the corresponding dihydroxy compound by acetylation with acetic anhydride and 0.1 ml of concentrated sulphuric acid at 20° C. After 1 hour the solution was poured into ice cold water and stirred for 16 hours. The suspension thus obtained was extracted into ethyl acetate, dried (Na$_2$SO$_4$) and concentrated. Trituration with ether gave 3,4-diacetoxy (5-methoxyimino) benzoic acid mp 160–164. NMR (DMSOd$_6$) 2.34(s, 3H); 2.38(s, 3H); 3.95(s, 3H); 7.8(d, 1H); 8.15(d, 1H); 8.26(s, 1H); 13.08(bs, 1H);
2. The starting material for this preparation was 3,4-dihydroxy 5-(1-t-butoxycarbonyl-1-methoxyimino)benzoic acid. Using the general procedure outlined above the activated ester was obtained and reacted with the appropriate cephalosporin to give the protected compound which was deprotected by treatment with 90% trifluoroacetic acid in water at 0° C. for 2 hours.
The crude product was purified according to the general procedure to give the title compound.

TABLE 2

NMR Data for compounds of Table 1 taken at 250 MHz in DMSOd$_6$/CF$_3$CO$_2$D (unless indicated)

| Example No. | |
|---|---|
| 1 | 1.50(s,3H); 1.53(s,3H); 3.53(dd,2H); 4.25(dd,1H); 4.42(dd,1H); 5.13(d,1H); 5.80(dd,1H); 7.01 s,1H); 7.3 (d,1H); 7.48(d,1H); 8.3(s,1H); 8.6(bt,1H); 9.62(d,1H). |
| 2 | 1.50(s,3H); 1.53(s,3H); 3.53(dd,2H); 3.85(s,3H); 4.15(dd,1H); 4.45(dd,1H); 5.15(d,1H); 5.80(dd,2H); 7.03(s,1H); 7.32(d,1H); 7.57(d,1H); 8.34(s,1H); 8.61 (bt,1H); 9.67(d,1H). |
| 3 | 1.50(s,3H); 1.53(s,3H); 3.50(dd,2H); 4.11(dd,1H); 4.42(dd,1H); 5.15(m,3H); 5.80(dd,1H); 7.01(s,1H); 7.3–7.6(m,7H); 8.42(s,1H); 8.60(bt,1H); 9.65(d,1H). |
| 4 | 1.50(s,3H); 1.54(s,3H); 3.50(dd,2H); 4.11(dd,1H); 4.42(dd,1H); 4.66(s,2H); 5.15(d,1H); 5.80(dd,1H); 7.03(s,1H); 7.35(d,1H); 7.55(d,1H); 8.44(s,1H); 8.64 (bt,1H); 9.65(d,1H). |
| 5 | 1.23(t,3H); 3.50(dd,2H); 4.08–4.3(m,3H); 4.42(dd,1H); 4.66(s,2H); 5.15(d,1H); 5.75(dd,1H); 6.97(s,1H); 7.34 (d,1H); 7.58(s,1H); 8.44(s,1H); 8.67(bt,1H); 9.8(d,1H). |
| 6 | 1.23(s,3H); 3.53(dd,2H); 4.2(dd,1H); 4.42(dd,1H); 5.15(d,1H); 5.80(dd,1H); 7.03(1H,s); 7.15–7.7(m,7H); 8.65(bt,1H); 9.65(d,1H). |
| 7 | 1.5(s,3H); 1.53(s,3H); 3.53(dd,2H); 4.16(dd,1H); 4.43(dd,1H); 5.16(d,1H); 5.81 (dd,1H); 6.75(t,1H); 6.95 (d,2H); 7.03(s,1H); 7.22(t,2H); 7.28(d,1H); 7.54(d,1H); 8.12(s,1H); 8.63(bt,1H); 9.65(d,1H). |
| 8 | 1.50(s,3H); 1.53(s,3H); 3.53(dd,2H); 4.05(dd,1H); 4.43(dd,1H); 5.06(s,2H); 5.15(d,1H); 5.81(dd,1H); 6.95(s,1H); 7.05(s,1H); 7.20–7.40(m,6H); 8.4(s,1H); 8.55(bt,1H); 9.65(d,1H). |
| 9 | 1.50(s,3H); 1.53(s,3H); 3.55(dd,2H); 4.05(dd,1H); 4.4–4.6(m,3H); 5.1–5.35(m,3H); 5.8(dd,1H); 5.83–6.1(m,1H); 6.97(s,1H); 7.05(s,1H); 7.26(s,1H); 8.34(s,1H); 8.50 (bt,1H); 9.65(d,1H). |
| 10 | 1.50(s,3H); 1.53(s,3H); 3.53(dd,2H); 4.04(dd.1H); 4.44(dd,1H); 5.12(d,1H); 5.32(s,2H); 5.80(dd.1H); 6.91(s,1H); 7.03(s,1H); 7.23 (s,1H); 7.28–7.50(m,4H); 8.30(s,1H); 8.51(bt,1H); 9.65(d,1H). |
| 11 | 0.80(t,3H); 1.30(m,10H); 3.52(dd,2H); 4.00(t,2H); 4.05(dd,1H); 4.44(dd,1H); 5.15(d,1H); 5.80(dd,1H); 6.93(s,1H); 7.04(s,1H); 7.28(s,1H); 8.30(s,1H); 8.52 (bt,1H); 9.65(d,1H). |
| 12 | (DMSO-d$_6$/CD$_3$COOD) 1.42(s,3H); 1.44(s,3H); 3.40 (dd,1H); 3.52(dd,1H); 4.18(dd,1H); 4.37(dd,1H); 5.05 (d,1H); 5.13(s,2H); 5.80(d,1H); 6.73(s,1H); 7.10–7.35 (m,6H); 7.78(s,1H); 7.80(d,1H). |

The activated esters for preparing the compounds of Examples 1 to 12 were obtained from the corresponding benzoic acids as described.

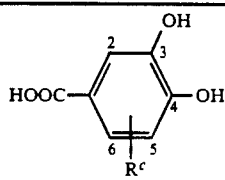

| Example | R$^c$ | Melting Point | NMR (DMSO-d$_6$) | Footnote |
|---------|-------|---------------|-------------------|----------|
| 1 | —CH=N—OH | 258–261 (dec) | 7.35(d, 1H); 7.60 (d, 1H); 8.35(s, 1H); | 1 |

-continued

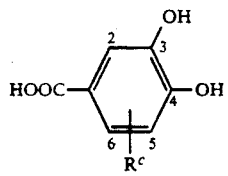

| Example | $R^c$ | Melting Point | NMR (DMSO-$d_6$) | Footnote |
|---|---|---|---|---|
|  |  |  | 10.06(bs, 1H); 10.26(s, 1H);11.3 (bs, 1H). |  |
| 2 | —CH=N—OMe | 230–3 | 3.93(s, 3H); 7.39 (d, 1H); 7.45(d, 1H); 8.35(s, 1H); 9.89 (bs, 2H); 12.56 (bs, 1H). | 1 |
| 3 | —CH=N—OCH$_2$Ph | 186–190 | 5.18(s, 3H); 7.32–7.42(m, 6H); 7.65 (d, 1H); 8.43(s, 1H); 9.89(bs, 2H); 12.55 (bs, 1H) | 1 |
| 4, 5 | —CH=N—OCH$_2$CO$_2$Bu$^t$ | 182–3 (dec) | 1.45(bs, 9H); 4.63 (s, 2H); 7.40(d, 1H); 7.68(d, 1H); 8.47 (s, 1H); 9.90 (bs, 1H); 10.00 (bs, 1H); 12.59 (bs, 1H). | 2 |
| 6 | —CH=CHPh | 235–239 | 7.10–7.6(m, 8H); 7.7(d, 1H); 9.40 (bs, 1H); 9.80 (bs, 1H). | 3 |
| 7 | —CH=NH—NHPh | 220–223 | 6.8(t, 1H); 7.0 (d, 2H); 7.26(t, 2H); 7.32(d, 1H); 7.68 (d, 1H); 8.18(s, 1H); 9.6(s, 1H); 10.45 (s, 1H); 10.65 (s, 1H); 12.5(bs, 1H) | 4 |
| 8 | —CH=N—OCH$_2$Ph | 152–156 | 5.13(s, 2H); 7.20 (s, 1H); 7.35–7.40 (m, 6H); 8.85(s, 1H); 9.6(bs, 1H); 9.8 (bs, 1H); 12.58 (bs, 1H). | 1 |
| 9 | —CH=N—OCH$_2$CHCH$_2$ | 208–211 | 4.5–4.65(m, 2H); 5.18–5.40(m, 2H); 5.80–6.20(m, 1H); 7.20(s, 1H); 7.36 (s, 1H); 8.82(s, 1H); 9.60(bs, 1H); 9.88 (bs, 1H); 12.72 (bs, 1H). | 1 |
| 10 | —CH=N—OCH$_2$-(2,6-dichlorophenyl) | 221–224 | 5.38(s, 2H); 7.20 (s, 1H); 7.35–7.55 (m, 4H); 8.85(s, 1H); 9.77(bs, 1H); 9.90 (bs, 1H); 12.75 (bs, 1H). | 1, 5 |
| 11 | CH=NOBu$^n$ | 161–163 | 0.80(t, 3H); 1.20–1.60(m, 4H); 4.00 (t, 2H); 7.18(s, 1H); 7.24(s, 1H); 8.75 (s, 1H); 10.04 (bs, 3H). | 1, 5 |

-continued

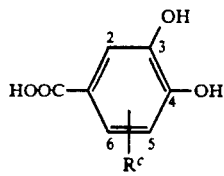

| Example | $R^c$ | Melting Point | NMR (DMSO-$d_6$) | Footnote |
|---------|-------|---------------|------------------|----------|
| 12 | —CH=N—N—CONH₂<br>　　　　\|<br>　　　　CH₂Ph | | 5.16(s, 2H); 6.80 (s, 2H); 7.15–7.40 (m, 6H); 7.80(m, 2H); 9.60(s, 1H); 9.80 (s, 1H); 12.45 (brs, 1H). | 6 |

Footnotes to Table 3

1. The appropriate oxime was prepared from 3,4-dihydroxy-5-formyl benzoic acid and the corresponding hydroxylamine hydrochloride by stirring in 10% aqueous sodium bicarbonate/methanol solution for 2–6 hours at room temperature. The product was isolated by diluting the reaction mixture with water (X 10) and then acidifying the diluted solution to pH 2 with 6NHCl. The resultant precipitate was filtered off and recrystallized from ethanol/water.

2. To a stirred solution of 3,4-dihydroxy-5-formyl benzoic acid (5 ml) in dimethylformamide (5 ml) was added pyridine (5.37 mM) and 4N HCl (5.5 mM) followed by the dropwise addition of t-butyl-2-aminoxyacetate (5 mM). The mixture was stirred at 20° C. for 2 hours and then diluted with water (50 ml). The mixture was acidified to pH 2 with 2NHCl and extracted into ethyl acetate (3 × 25 ml). The combined extracts were washed with water, dried and evaporated to give the title compound which was crystallized from ethyl acetate/petrol (60–80).

3. To a stirred suspension of benzyltriphenyl phosphonium chloride (4.9 g. 12.6 mM) in tetrahydrofuran (80 ml) under argon at 0–5° C. was added dropwise 1.6M n-butyl lithium (8.06 mls, 12.9 mM). A dark red solution was formed and after 30 minutes methyl 3,4-dimethoxy-5-formylbenzoate (12.9 mM) in tetrahydrofuran was added dropwise over 10 minutes. The reaction mixture was refluxed for 3 hours and then cooled.

The reaction mixture was diluted with aqueous ammonium chloride solution (1% solution, 500 ml) and then extracted with ethyl acetate (3 × 200 ml). The combined extracts were washed with water, dried and evaporated to give an oil which was triturated with ether to give triphenyl phosphine oxide which was removed by filtration. The filtrate was chromatographed by silica gel flash chromatography using 60–80 petrol/ethylacetate 4:1 as eluting solvent to give methyl-3,4,dimethoxy-5- (2-phenylethenyl)benzoate.

The product (1.2 g) was dissolved in dichloromethane (50 ml) and boron tribromide (1M) (25 ml) was slowly added at 0° C. and under anatmosphere of argon. The reaction mixture was stirred overnight at 20° C. and then poured into an ice-cold solution of sodium bicarbonate. Dichloromethane was removed by rotary evaporation and the clear solution was then acidified to pH 2 with 6NHCl. The mixture was then extracted with ethyl acetate (3 × 100 ml) and the combined extracts were washed with water, dried and evaporated to give a yellow brown solid (1.1 g) which was triturated with ether/toluene to give 3,4-dihydroxy 5-(2-phenylethenyl)benzoic acid.

4. 3,4-Dihydroxy-5-formyl benzoic acid (5 mM) and phenyl hydrazine (5.5 mM) were dissolved in ethanol (7 ml) and heated at 100° C. for 15 minutes. The reaction mixture was concentrated to dryness and the frothy residue thus obtained was triturated with ether to provide a crude product which was crystallized from ethyl acetate to give the desired compound.

5. The crude product was further purified by flash chromatography on silica gel using a mixture of ethyl acetate, 60–80 petroleum ether and acetic acid (13.5:6:0.5) as eluting solvent. The fractions containing the desired product were concentrated and the residual acid was crystallized from ether/toluene to give the title compound.

6. 3,4-Dihydroxy-5-formyl benzoic acid (364 mg) in methanol (6 ml) was stirred with benzyl semicarbazide (330 mg) for 30 minutes at room temperature. A cream precipitate formed and was collected by filtration after 2 hours stirring.

EXAMPLES 13-15

To a stirred solution of 2-phenylazo-3,4-dihydroxypyridin-6-carboxylic acid (0.6 mM) and N-hydroxysuccinimide (0.6 mM) in dimethylsulphoxide (2 ml) was added dicyclohexylcarbodi-imide (0.6 mM) and the mixture was stirred for 1 hour at room temperature. This mixture was subsequently added to a stirred, partial solution of the appropriate 3-aminomethyl cephalosporin (0.5 mM) and triethylamine (0.1 mM) in dimethylsulphoxide (2 ml) and the mixture was stirred for a further 2 hours.

The reaction mixture was acidified with glacial acetic acid, diluted with water (approx. 20 ml), sodium acetate (1 g) was added and the mixture filtered and the filtrate was purified by medium pressure chromatography on HP2OSS resin (gradient eluting with aqueous acetonitrile). The product was collected, acetonitrile removed by evaporation and the residue was freeze-dried, triturated with ether and dried under vacuum.

Using the appropriate precursors the compounds of Examples 14 and 15 were obtained in analogous manner.

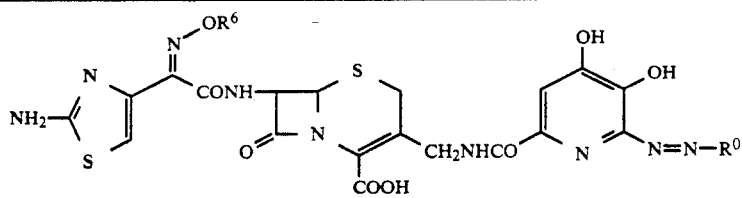

| Ex. | R | $R^0$ | Footnote | NMR Data (DMSO-$d_6$/CD$_3$COOD) |
|---|---|---|---|---|
| 13 | C(CH$_3$)$_2$COOH | Ph | 1 | 1.15(t, 18H); 1.50(d, 6H); 3.08(q, 12H); 3.60(q, 2H); 4.08(q, 1H); 4.50(q, 1H); 5.16(d, 1H); 5.82(q, 1H); 7.02(s, 1H); 7.60(m, 4H); 8.00(m, 2H); MS. FAB (M − H)724. |
| 14 | CH$_2$CH$_3$ | Ph | 2 | 1.15(t, 9H); 1.25(t, 3H); 3.08(q, 6H); 3.58(q, 2H); 4.06(q, 1H); 4.50(q, 1H); 4.20(q, 2H); 5.15(d, 1H); 5.78(q, 1H); 6.96(s, 1H); 7.60(m, 4H); 8.02(m, 2H); MS. FAB (M + H) 668 |
| 15 | C(CH$_3$)$_2$COOH | 2,4,6-trimethylphenyl | 2 | 1.12(t, 9H); 1.50(d, 6H); 2.39(s, 9H); 3.04(m, 6H); 3.60(t, 2H); 4.06(q, 1H); 4.48(q, 1H); 5.15(d, 1H); 5.82(q, 1H); 7.00(s, 1H); 7.02(s, 2H); 7.60(s, 1H); MS FAB (M − H) 766. |

Footnotes
1. Bis-triethylamine salt formed.
2. Mono-triethylamine salt formed.

The cephalosporin starting-materials are known from EP-A-127992 and EP-A-164944.

The pyridine carboxylic acid starting-materials were prepared as follows:

To a stirred solution of aniline (11 mM) in 2N HCl (11 ml) at 0° C., was slowly added a solution of sodium nitrate (11 mM) in water (1 ml). The solution was stirred for 10 minutes and was then slowly added to a stirred solution of comenamic acid (10 mM) in 2.5N NaOH (20 ml) at 0° C. Water (20 ml) was added during the addition to assist stirring. The mixture was stirred for 2 hours.

The solution was extracted with ethyl acetate and the organic phase was discarded. The aqueous phase was acidified to pH2, precipitating the product as a semi-solid mass. The suspension was stirred with ethyl acetate and the two-phase mixture was filtered. The product was washed with water, followed by a little ethyl acetate and then dried under vacuum; NMR (DMSO-$d_6$) 7.50(s,1H); 7.65(m,3H); 8.05(m,2H): MS. FAB (M−H) 258.

In analogous manner 2,4,6-trimethylaniline gave 2-(2,4,6-trimethylphenylazo)-3,4-dihydroxypyridin-6-carboxylic acid; NMR (DMSO-$d_6$) 2.50(s,9H); 7.02(s,2H); 7.41(s,1H); MS FAB (M−H) 300.

We claim:

1. A compound of the formula (III):

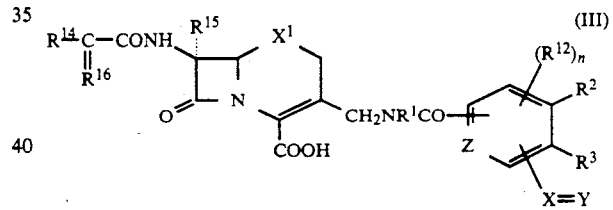

or a salt or ester thereof wherein $R^1$ is hydrogen, C$_{1-6}$ alkyl optionally substituted by any of halo, hydroxy, C$_{1-6}$ alkoxy, carboxy, amino, cyano, C$_{1-6}$ alkanoylamino, phenyl or heteroaryl, or $R^1$ is C$_{2-6}$ alkenyl; $R^2$ is hydroxy or an in vivo hydrolysable ester thereof; $R^3$ is hydroxy or an in vivo hydrolysable ester thereof;

Z is CH or N;

X is a group CR$^4$, wherein R$^4$ is hydrogen, optionally substituted C$_{1-6}$alkyl, aryl, acrylC$_{1-6}$alkyl, heteroaryl or heteroaryl C$_{1-6}$ alkyl;

Y is a group NOR$^5$, NNR$^{51}$R$^6$, NR$_7$ (when —X=Y is ortho to a hydroxy group) or CR$^{8R9}$, wherein R$^5$ is hydrogen, optionally substituted C$_{1-6}$ alkyl, arylC$_{1-6}$ alkyl, heteroaryl C$_{1-6}$ alkyl, optionally substituted C$_{2-6}$ alkenyl, optionally substituted C$_{3-7}$ cycloalkyl, aryl or heteroaryl; R$^{51}$ is hydrogen, optionally substituted C$_{1-6}$ alkyl, arylC$_{1-6}$alkyl, heteroarylC$_{1-6}$alkyl, optionally substituted C$_{2-6}$ alkenyl, optionally substituted C$_{3-7}$cycloalkyl, aryl, heteroaryl, C$_{1-6}$alkanoyl, arylC$_{1-6}$alkanoyl, heteroarylC$_{1-6}$ alkanoyl, C$_{2-6}$alkenoyl, C$_{3-7}$cycloalkylcarbonyl, arylcarbonyl, heteroarylcarbonyl, carbamoyl, C$_{1-6}$alkylcarbamoyl, arylcarbamoyl or arylC$_{1-6}$ alkylcarbamoyl; R$^6$ is hydrogen, C$_{1-6}$ alkyl or arylC$_{1-6}$ alkyl; $R^7$ is optionally substituted $C_{1-6}$alkyl, aryl$C_{1-6}$alkyl, heteroaryl $C_{1-6}$ alkyl, optionally substituted $C_{2-6}$ alkenyl, $C_{3-7}$ cycloalkyl, aryl or heteroaryl; $R^8$ and $R^9$ are independently halogen, hydrogen, optionally substituted $C_{2-6}$ alkyl, aryl$C_{1-6}$alkyl, heteroaryl$C_{1-6}$alkyl, optionally substituted $C_{2-6}$ alkenyl, $C_{3-7}$cycloalkyl, aryl, heteroaryl, optionally substituted $C_{1-6}$ alkanoyl, optionally substituted $C_{1-6}$ alkoxycarbonyl, carboxy, arylcarbonyl, heteroarylcarbonyl or aryl $C_{1-6}$ alkoxycarbonyl;

or X=Y is a group $-N=N-R^{10}$ or, when Z is N, X=Y is also a group $-N=CR^{10}R^{11}$ wherein $R^{10}$ is optionally substituted aryl and $R^{11}$ is hydrogen or $C_{1-6}$alkyl;

$R^{12}$ is $C_{1-6}$ alkyl, halo, hydroxy, hydroxy $C_{1-6}$alkyl, cyano, trifluoromethyl, nitro, amino, $C_{1-6}$ alkylamino, di-$C_{1-6}$ alkylamino, $C_{1-6}$alkanoyl, $C_{1-6}$ alkoxy, $C_{1-6}$ alkylthio, $C_{1-6}$ alkanoyloxy, carbamoyl, $C_{1-6}$ alkylcarbamoyl, di-$C_{1-6}$ alkylcarbamoyl, carboxy, carboxy $C_{1-6}$ alkyl, $C_{1-6}$alkoxycarbonyl$C_{1-6}$alkyl, sulpho, sulpho$C_{1-6}$ alkyl, $C_{1-6}$ alkane-sulphonamido, $C_{1-6}$ alkoxycarbonyl, $C_{1-6}$ alkanoylamino, thioureido or amidino, and n is zero to 2, the optional substitution in $R^4$ being hydroxy, halo, $C_{1-6}$ alkoxy, amino, $C_{1-6}$ alkylamino or di-$C_{1-6}$ alkylamino;

the optional substitution in $R^5$ being hydroxy, $C_{1-6}$ alkoxy, halo, carboxy, $C_{1-4}$ alkylcarbamoyl, $C_{1-6}$ alkylthio, $C_{1-6}$ alkylamino, di-$C_{1-6}$ alkylamino, cyano, $C_{1-6}$alkanesulphonamido, $C_{1-6}$alkoxycarbonyl or alkanoyl;

the optional substitution for $C_{1-6}$ alkyl, $C_{2-6}$ alkanoyl and $C_{3-7}$ cycloalkyl in $R^{51}$ being hydroxy, $C_{1-6}$ alkoxy, halo, carboxy, $C_{1-4}$ alkylcarbamoyl, di-$C_{1-6}$ alkylcarbamoyl, $C_{1-6}$ alkylthio, amino, $C_{1-6}$ alkylamino, di-$C_{1-6}$ alkylamino, cyano, $C_{1-6}$ alkanesulphonamido, $C_{1-6}$ alkoxycarbonyl or $C_{1-6}$ alkanoyl;

the optional substitution in $R^7$ for $C_{1-6}$ alkyl and $C_{2-6}$ alkenyl being hydroxy, $C_{1-6}$ alkoxy, halo, carboxy, $C_{1-4}$ alkylcarbamoyl, di-$C_{1-6}$ alkylcarbamoyl, di-$C_{1-6}$alkythio, amino, $C_{1-6}$alkylamino, di-$C_{1-6}$alkylamino, cyano, $C_{1-6}$ alkanesulphonamido, $C_{1-6}$ alkoxycarbonyl or $C_{1-6}$ alkanoyl;

the optional substitution for $C_{1-6}$ alkyl, $C_{2-6}$ alkenyl, $C_{1-6}$ alkanoyl and $C_{1-6}$ alkylcarbonyl in $R^8$ and $R^9$ being hydroxy, $C_{1-6}$ alkoxy, halo, carboxy, $C_{1-4}$ alkylcarbamoyl, di-$C_{1-6}$ alkylcarbamoyl, $C_{1-6}$ alkylthio, amino, $C_{1-6}$ alkylamino, di-$C_{1-6}$ alkylamino, cyano, $C_{1-6}$ alkanesulphonamido, $C_{1-6}$ alkoxycarbonyl or $C_{1-6}$ alkanoyl;

the optional substitution for aryl in $R^{10}$ being hydroxy, $C_{1-6}$ alkoxy, cyano, nitro, $C_{1-6}$ alkyl or $C_{1-6}$ alkylthio;

heteroaryl being a 5- or 6-membered ring containing 1 to 3 atoms selected from nitrogen, oxygen and sulphur optionally substituted by $R^{12}$; and aryl, when other than $R^{10}$, being phenyl or naphthyl optionally substituted by $R^{12}$; $X^1$ is sulphur or sulphinyl; $R^{15}$ is hydrogen, methoxy or formamido;

$R^{14}$ is 2-aminothiazol-4-yl or 2-aminoooxazol-4-yl each optionally substituted in the 5-position by fluorine, chlorine or bromine, or $R^{14}$ is 5-aminisothiazol-3-yl, 5-amino-1,2,4-thiadiazol-3-yl, 3-aminopyrazol-5-yl, 3-aminopyrazol-4-yl, 2-aminopyrimidin-5-yl, 2-aminopyrid-6-yl, 4-aminopyrimidin-2-yl, 2-amino-1,3,4-thiadiazol-5-yl or 5-amino-1-methyl-1,2,4-triazol-3-yl $R^{16}$ is of the formula $=N.O.R^{17}$ (having the syn configuration about the double bond) wherein $R^{17}$ is hydrogen, (1-6C)alkyl, (3-8C)cycloalkyl, (1-3C)alkyl(3-6C)cycloalkyl, (3-6C)cycloalkyl(1-3C)alkyl, (3-6C)alkenyl, optionally substituted by carboxy, (5-8C)cycloalkenyl, (3-6C)alkynyl, (2-5C)alkylcarbamoyl, phenylcarbamoyl, benzylcarbamoyl, (1-4C) alkylcarbamoyl (1-4C)alkyl, di(1-4Calkylcarbamoyl (1-4C)alkyl, (1-4C)haloalkylcarbamoyl(1-4C)alkyl, (1-3C)haloalyl, (2-6C)hydroxyalkyl, (1-4C)alkoxy(2-4C)alkyl, (1-4C)alkylthio(2-4C)alkyl, (1-4C)alkanesuphinyl (1-4C)alkyl, (1-4C)alkanesulphonyl(1-4C)alkyl, (2-6C)aminoalkyl, (1-4C)alkylamino(1-6C)alkyl, (2-8C)dialkylamino(2-6C)alkyl, (1-5C)cyanoalkyl, 3-amino-3-carboxypropyl, 2-(amidinothio)ethyl, 2-(N-aminoamidinothio)ethyl, tetrahydropyran-2-yl, thietan-3-yl, 2-oxopyrrolidinyl, or 2-oxotetrahydrofuranyl, or $R^{17}$ is of the formula IV:

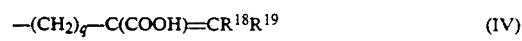

wherein q is one or two and $R^{18}$ and $R^{19}$ are independently hydrogen or $C_{1-4}$alkyl; or $R^{17}$ is of the formula V:

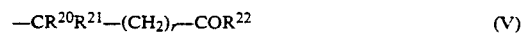

wherein r is 0-3, $R^{20}$ is hydrogen, (1-3C)alkyl or methylthio, $R^{21}$ is hydrogen, (1-3C) alkyl, (3-7C) cycloalkyl, cyano, carboxy, (2-5C)carboxyalkyl or methanesulphonylamino, or $R^{20}$ and $R^{21}$ are joined to form, together with the carbon to which they are attached, a (3-7C) carbocyclic ring, and $R^{22}$ is hydroxy, amino, (1-4C)alkoxy, (1-4C) alkylamino or of the formula NHOR$^{23}$ in which $R^{23}$ is hydrogen or (1-4C)alkyl;

or $R^{16}$ may be of the formula $=CH.R^{24}$ wherein $R^{24}$ is hydrogen, halogen, (1-6C)alkyl, (3-7C) cycloalkyl, (2-6C)alkenyl, (3-7C)cycloalkenyl, phenyl or benzyl.

2. A compound according to claim 1 wherein $R^2$ and $R^3$ are both hydroxy.

3. A compound according to claim 1 wherein the cephalosporin compound has a 3-position substituent of the formula (II):

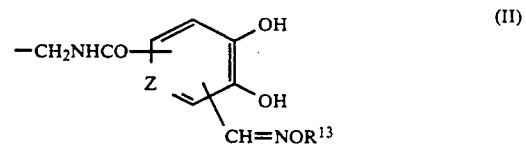

wherein Z is $-CH=$ or $-N=$ and $R^{13}$ is hydrogen, $C_{1-6}$alkyl, benzyl, carboxy$C_{1-6}$alkyl or allyl.

4. A compound according to claim 1 wherein the cephalosporin compound has a 3-position substituent of the formula (IIa):

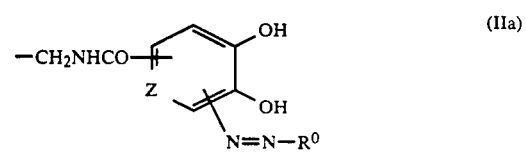

wherein Z is $-CH=$ or $-N=$ and $R^0$ is phenyl or 2,4,6-trimethylphenol.

5. A compound according to claim 1 wherein $R^{17}$ is 2-carboxyprop-2-yl.

6. A compound according to claim 1 which is:

7-[2-(2-aminothiazol-4-yl)-2-((Z)-1-carboxy-1-methylethoxyimino)acetamido]-3-((3,4-dihydroxy-5-hydroxyimino)benzoylaminomethyl)ceph-3-em-4-carboxylic acid, 7[2-(2-aminothiazol-4-yl)-2-((Z)-1-carboxy-1methylethoxyimino)acetamido]-3-((3,4-dihydroxy-5-methoxyimino)benzoylaminomethyl)ceph-3-em-4-carboxylic acid, acid, 7[2-(2-aminothiazol-4-yl)-2-((Z)-1-carboxy-1methylethoxyimino)acetamido]-3-((3,4-dihydroxy-5-benzyloxyimino)benzoylaminomethyl)ceph-3em-4-carboxylic acid, 7[2-(2-aminothiazol-4-yl)-2-((Z)-1-carboxy-1methylethoxyimino)acetamido]-3-((3,4-dihydroxy-5-carboxymethoxyimino)benzoylaminomethyl)ceph-3-em-4-carboxylic acid, 7[2-(2-aminothiazol-4-yl)-2-((Z)-1-carboxy-1methylethoxyimino)acetamido]-3-((3,4-dihydroxy-6-benzyloxyimino)benzoylaminomethyl)ceph-3-em-4-carboxylic acid, 7[2-(2-aminothiazol-4-yl)-2-((Z)-1-carboxy-1methylethoxyimino)acetamido]-3-((3,4-dihydroxy-6-allyloxyimino)benzoylaminomethyl)ceph-3-em-4-carboxylic acid, 7[2-(2-aminothiazol-4-yl)-2-((Z)-1-carboxy-1methylethoxyimino)acetamido]-3-((3,4-dihydroxy-6-n-butoxyimino)benzoylaminomethyl)ceph-3-em-4-carboxylic acid, or 7[2-(2-aminothiazol-4-yl)-2-((Z)-1-carboxy-1methylethoxyimino)acetamido]-3-((3,4-dihydroxy-5-cinnamyl)benzoylaminomethyl)ceph-3-em-4-carboxylic acid.

7. A pharmaceutical composition which comprises a compound according to claim 1 and a pharmaceutically acceptable carrier.

8. A method of treating a bacterial infection in a mammal which comprises administering thereto an effective amount of a compound according to claim 1.

* * * * *